(12) United States Patent
Gouvea et al.

(10) Patent No.: US 11,306,337 B2
(45) Date of Patent: Apr. 19, 2022

(54) POLYPEPTIDES HAVING HYDROLYTIC ACTIVITY ON 1-KESTOSE IN THE PRESENCE OF SUCROSE BUT LACKING SUCRASE (INVERTASE) ACTIVITY, POLYNUCLEOTIDES ENCODING SAME AND METHODS OF PRODUCING AND USING SAME IN INDUSTRIAL SUCROSE PRODUCTION FROM 1-KESTOSE

(71) Applicant: CTC—Centro de Tecnologia Canavieira S.A., Piracicaba (BR)

(72) Inventors: Iuri Estrada Gouvea, São Paulo (BR); Cesar Moises Camilo, São Paulo (BR); Jaime Finguerut, São Paulo (BR); Michael Cook, São Paulo (BR)

(73) Assignee: CTC—Centro de Tecnologia Canavieira S.A., Piracicaba (BR)

( * ) Notice: Subject to any disclaimer, the term of this patent is extended or adjusted under 35 U.S.C. 154(b) by 0 days.

(21) Appl. No.: 15/775,690

(22) PCT Filed: Nov. 11, 2016

(86) PCT No.: PCT/BR2016/050295
§ 371 (c)(1),
(2) Date: May 11, 2018

(87) PCT Pub. No.: WO2017/079818
PCT Pub. Date: May 18, 2017

(65) Prior Publication Data
US 2019/0276864 A1    Sep. 12, 2019

Related U.S. Application Data

(60) Provisional application No. 62/254,501, filed on Nov. 12, 2015.

(51) Int. Cl.
*C12P 19/12* (2006.01)
*C12P 19/14* (2006.01)
(Continued)

(52) U.S. Cl.
CPC ............ *C12P 19/12* (2013.01); *C12N 9/2402* (2013.01); *C12P 19/02* (2013.01); *C12P 19/14* (2013.01); *C13B 20/002* (2013.01)

(58) Field of Classification Search
None
See application file for complete search history.

(56) References Cited

U.S. PATENT DOCUMENTS

| 5,463,038 A | 10/1995 | Hidano | |
| 2011/0201059 A1* | 8/2011 | Hall | C12N 15/8245 435/96 |
| 2019/0276864 A1* | 9/2019 | Gouvea | C12P 19/02 |

FOREIGN PATENT DOCUMENTS

| WO | 9601904 A1 | 1/1996 |
| WO | 9621023 A1 | 7/1996 |

(Continued)

OTHER PUBLICATIONS

Xu et al., "Cloning and functional characterization of two abiotic stress-responsive Jerusalem artichoke (*Helianthus tuberosus*) fructan 1-exohydrolases (1-FEHs)", Plant Molecular Biology, vol. 87, pp. 81-98, 2015 (Year: 2015).*

(Continued)

*Primary Examiner* — Richard C Ekstrom
(74) *Attorney, Agent, or Firm* — Laurence P. Colton; Smith Tempel Blaha LLC

(57) ABSTRACT

An industrial process using kestose hydrolases to enable the use of sugar mixtures containing 1-kestose in the industrial production of sucrose (as crystallized sugar) by providing a method for the conversion of 1-kestose into sucrose and (Continued)

fructose in a sugar solution, containing kestose and more than 10 mM sucrose (3 g/L), and comprising the enzymatic hydrolysis (preferably using 1-FEH enzymes—EC 3.2.1.153) of 1-kestose. The process further provides a method of producing a polypeptide having 1-kestose hydrolase activity and a composition comprising the polypeptide.

7 Claims, 4 Drawing Sheets

Specification includes a Sequence Listing.

(51) Int. Cl.
| | | |
|---|---|---|
| *C13B 20/00* | (2011.01) | |
| *C12N 9/24* | (2006.01) | |
| *C12P 19/02* | (2006.01) | |

(56) References Cited

FOREIGN PATENT DOCUMENTS

| WO | 9721718 A1 | 6/1997 |
| WO | 9839460 A1 | 9/1998 |
| WO | 9924593 A1 | 5/1999 |
| WO | 9931281 A1 | 6/1999 |
| WO | 2006066969 A1 | 6/2006 |
| WO | 2009152285 A1 | 12/2009 |

OTHER PUBLICATIONS

Verhaest et al., "Insights into the fine architecture of the active site of chicory fructan 1-exohydrolase: 1-kestose as substrate vs sucrose as inhibitor", New Phytologist, vol. 174, pp. 90-100, 2007 (Year: 2007).*

WIPO. International Search Report on parent application PCT/BR2016/050295, dated Feb. 15, 2017.
Sainz-Polo, M. A., et al., Three-Dimensional Structure of Saccharomyces Invertase: Role of a Non-Catalytic Domain in Oligomerization and Substrate Specificity. J. Bio. Chem.2013, vol. 288, No. 14. pp. 9755-9766.
Xu, H., et al.. Cloning and functional characterization of two abiotic stree-responsive Jerusalem artichoke (*Helianthus tuberosus*) fructan 1-exohydrolases (1-FEHs), Plant Mol. Biol., Jan. 2015, vol. 87, No. 1, pp. 81-98.
Verhaest, M., et al., Insights into the fine architecture of the active site of chicory fructan 1-exohydrolase: 1-kestose as substrate vs sucrose as inhibitor, New Phytol., 2007, vol. 174, No. 1. pp. 90-100.
Belhamri, R., et al., Effect of impurities on sucrose crystal shape and growth, Current Topics in Crystal Growth Research, 2004, vol. 7, pp. 63-70.
Le Roy, K., et al., Influencing the binding configuration of sucrose in the active sites of chicory fructan 1-exohydrolase and sugar beet fructan 6-exohydrolase, New Phytol., 2008, vol. 178, No. 3, pp. 572-580.
Van Der Ende, W. et al., Donor and acceptor substrate selectivity among plant glycoside hydrolase family 32 enzymes, FRBS J., 2009, vol. 276, No. 20, pp. 5788-5798.
Van Der Ende, W., et al., Fructan 1-exohydrolases. Beta-(2,1)-trimmers during graminan biosynthesis in stems of wheat? Purification, characterization, mass mapping, and cloning of two fructan 1-exohydrolase isoforms, Plant Physiol., 2003, vol. 131, No. 2, pp. 621-631.
Claessens, G., et al., Purification and Properties of an Inulinase from Chicory Roots (*Cichorium intybus* L.), J. Plant Physiol, 1990, vol. 136, No. 1, pp. 35-39.
De Cononck, B., et al., Arabidopsis AtcwlNV3 and 6 Are Not Invertases but Are Fructan Exohydrolases (FEHs) with Different Substrate Specificities, Plant, Cell and Environment, 2005, vol. 28, No. 4, pp. 432-443.

* cited by examiner

POLYPEPTIDES HAVING HYDROLYTIC ACTIVITY ON 1-KESTOSE IN THE PRESENCE OF SUCROSE BUT LACKING SUCRASE (INVERTASE) ACTIVITY, POLYNUCLEOTIDES ENCODING SAME AND METHODS OF PRODUCING AND USING SAME IN INDUSTRIAL SUCROSE PRODUCTION FROM 1-KESTOSE

CROSS-REFERENCE TO RELATED APPLICATIONS

This application is the US National Phase of International Application No. PCT/BR2016/050295 having an international filing date of 11 Nov. 2016, which claims priority on and the benefit of U.S. Provisional Patent Application No. 62/254,501 having a filing date of 12 Nov. 2015.

SEQUENCE LISTING

The instant application contains a Sequence Listing which has been submitted in ASCII format via EFS-Web and is hereby incorporated by reference in its entirety. Said ASCII copy, created on 12 Nov. 2020, is named 60752-003u1-seq-id.txt and is 30 kbytes in size.

BACKGROUND OF THE INVENTION

Technical Field

The present invention relates to the field of industrial sugar production. Particularly, the present invention relates to isolated polypeptides capable of hydrolyzing 1-kestose in the presence of sucrose but lacking sucrase (invertase) activity, and polynucleotides encoding the polypeptides. The invention also relates to nucleic acid constructs, vectors, and host cells comprising the polynucleotides as well as methods of producing and using the polypeptides in industrial sucrose production from 1-kestose and sugar solutions containing 1-kestose.

Prior Art

Industrial Sugar Production

Sugar (Sucrose) is produced in 120 countries and global production is currently around 180 million tons a year. Approximately 80% is produced from sugarcane while the remaining 20% is produced from sugar beet. For a general perspective, 70 countries produce sugar from sugarcane, 40 from sugar beet, and 10 from both. The 10 largest sugar-producing nations represent roughly 75% of world sugar production while Brazil alone accounts for almost 25% of world production.

While fructans are naturally found in very low concentration in sugarcane and sugar beet current biotechnological methods can allow the generation of sugarcane, sugar beet and other crop plants with an increased storage of carbohydrate content in the form of fructans. For example, the international patent applications WO96/01904, WO96/21023, WO98/39460, WO99/24593, WO2006066969 and WO2009152285 propose the expression of heterologous genes, alone or in combination, in sugarcane in order to produce and accumulate fructans in transgenic crops.

Inulin is a fructan type carbohydrate polymer, which occurs as a polydisperse composition in many plants and can also be produced by certain bacteria and fungi. Inulin from plant origin usually consists of a polydisperse composition of mainly linear chains composed of fructose units (mostly terminating in one glucose unit) which are linked to each other through beta (2-1) fructosyl-fructose linkages. The smallest inulin molecule, the trisaccharide 1-kestose (GFF; IUPAC NAME β-D-fructofuranosyl-(2→1)-β-D-fructofuranosyl α-D-glucopyranoside—structural formulae A) is identified as a key fructan type carbohydrate to be stored in transgenic crops. The present invention relates to juice of transgenic crops containing small fructans, particularly 1-kestose. 1-kestose and sucrose 2d chemical structures are represented by structural formulae (A) and (B), respectively:

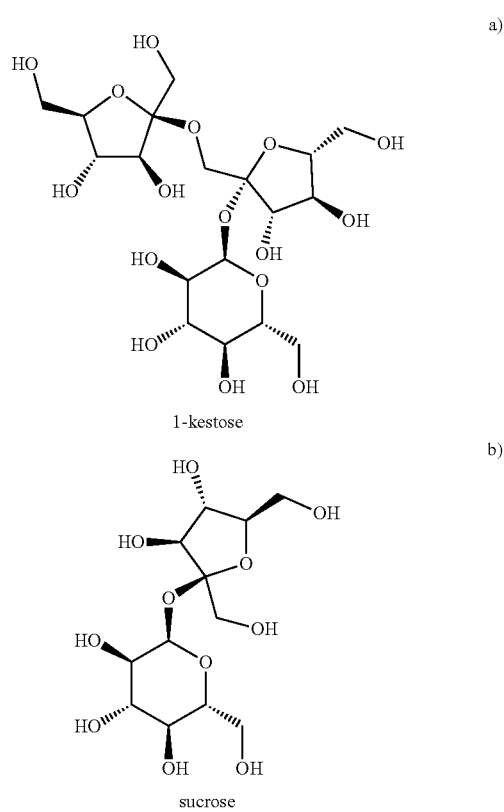

While the state-of-the-art indicates that the juice of transgenic crops with an increased carbohydrate content in the form of 1-kestose constitute an economically interesting starting material for fermentation products, of which *Saccharomyces cerevisiae* ethanol production is the most important, the industrial production of sucrose, as crystallized sugar, is in fact, expected to be hampered by 1-kestose.

Kestoses are considered as stable as sucrose and there are indications that oligosaccharides like raffinose from sugar beet, dextran from sugarcane and kestoses, as well as other associated oligosaccharides can cause crystal deformations (elongation of the B- or C-axis), and do impact sugar crystallization, the main purification procedure used to recover sucrose from the sugarcane or sugar beet plant extract.

It is known for a person skilled in the art that several factors can influence sugar crystal growth rates, including supersaturation, temperature variations and the concentration and nature of impurities. Factors that affect the efficiency of this operation can have implications for crystal recovery (yield). Modification in shape or appearance of sucrose crystal is related to crystal growth rates reductions.

This slows down industrial sugar production, effectively reducing factory capacity and leading to increased energy costs due to the longer processing times.

Since the currently available described methods for recovery or chromatographic separation of 1-kestose from sugar mixtures are extremely complex and unfeasible from the technical-economic-industrial point of view (U.S. Pat. No. 5,463,038, WO97/21718), the juice of the referred transgenic crops need to be segregated from sugar factories. The segregation is necessary in order to prevent contamination of the traditional crop sugarcane juice with the juice of 1-kestose rich transgenic crop, and avoid the resulting crystallization problems. In this way, this restriction ends up limiting the economic potential of using 1-kestose rich transgenic crop as starting material for fermentation products.

The present invention describes the use of specific enzymes (kestose hydrolases) in an economically viable process to enable the use of sugar mixtures containing 1-kestose in the industrial production of sucrose (as crystallized sugar).

Enzymes:

The enzymes responsible for hydrolyzing carbohydrates are namely glycoside hydrolases (GH) (glycosidases, O-glycoside hydrolases, EC 3.2.1.x). Based on common structural fold and amino acid sequence comparisons they are classified in families as described and according to the Carbohydrate-Active enZYme server (http://www.cazy.org/).

Glycoside hydrolase family GH32 contains one of the earliest described enzyme activities, namely that of 'inverting' sucrose, from which is derived the name of 'invertase' (EC 3.2.1.26). In addition to the 'historical' invertases, this family also contains enzymes that hydrolyze fructose containing polysaccharides such as inulinases (EC 3.2.1.7) and exo-inulinases (EC 3.2.1.80), levanases (EC 3.2.1.65) and β-2,6-fructan 6-levanbiohydrolases (EC 3.2.1.64), fructan β-(2,1)-fructosidase/1-exohydrolase (EC 3.2.1.153) or fructan β-(2,6)-fructosidase/6-exohydrolases (EC 3.2.1.154). In addition, GH32 family comprises enzymes displaying transglycosylating activities such as sucrose:sucrose 1-fructosyltransferases (EC 2.4.1.99), fructan:fructan 1-fructosyltransferase (EC 2.4.1.100), sucrose:fructan 6-fructosyltransferase (EC 2.4.1.10), fructan:fructan 6G-fructosyltransferase (EC 2.4.1.243) and levan fructosyltransferases (EC 2.4.1.-). All of these enzymes have a common β-propeller catalytic domain with three conserved amino acids, located in the deep axial pocket of the active site. The propeller has a 5-fold repeat of blades, each consisting of four antiparallel β-strands with the classical 'W' topology around the central axis, enclosing the negatively charged cavity of the active site.

In general, the catalytic reaction of GH32 enzymes occurs by a retaining mechanism in which an aspartate (Asp/D) located close to the N terminus acts as the nucleophile and a glutamate (Glu/E) acts as the general acid/base catalyst. The reaction proceeds through attachment of the aspartate nucleophile to a fructosyl unit of the donor substrate. The fructosyl is subsequently released by hydrolysis (or transferred to an acceptor sugar substrate in transglycosylation). The present invention relates to fructosyl hydrolysis, particularly the hydrolysis of terminal, non-reducing (2→1)-beta-D-fructofuranose residues in oligosaccharides.

In the case of *Saccharomyces cerevisiae* invertase, the prototype of EC 3.2.1.26, dimerization plays a determinant role in substrate specificity, preventing binding of extended substrates, which explains its invertase character at the molecular level (Sainz-Polo et al. 2013). As extracted from the work of Sainz-Polo and colleagues, when comparing the activity of *S. cerevisiae* invertase with different oligosaccharides, the highest efficiency was found with sucrose as a substrate, followed by the trisaccharides raffinose and 1-kestose, whereas the tetrasaccharide nystose was hydrolyzed at a much lower rate. No significant activity was observed with inulin as the substrate (Table 1).

TABLE 1

Comparative substrate Specificity of *Saccharomyces cerevisiae* invertase. Data extracted from Sainz-Polo et al., 2013.

| Substrate | Activity µmol/min/mg |
|---|---|
| Sucrose | 520 ± 20 |
| 1-Kestose | 102 ± 11 |
| Raffinose | 187 ± 8 |
| Nystose | 36 ± 1 |
| Inulin | 2.5 ± 0.1 |

Exo-inulinases or fructan beta-fructosidase (EC 3.2.1.80), found in Bacteria and Eukaryota domains, hydrolyses terminal, non-reducing (2→1)- and (2→6)-linked beta-D-fructofuranose residues in fructans like inulin, levan, kestose and sucrose. As general rule, they hydrolyze inulin and sucrose with similar efficiency and are economically important to industrial production of high fructose syrup from natural inulins.

On the other hand, Fructan 1-exohydrolase (1-FEH/Fructan beta-(2,1)-fructosidase—EC 3.2.1.153) were only reported in Magnoliophyta division of plants so far (i.e., angiosperms, including crops, grains, grasses, garden and roadside weeds, and broad-leaved trees and shrubs). While these plant enzymes also promote hydrolysis of terminal, non-reducing (2→1)-linked beta-D-fructofuranose residues in fructans, they are distinguished from exo-inulinases (EC 3.2.1.80) by the fact that they have no or have very low activity against sucrose.

The present invention relates to fructosyl hydrolysis, particularly the hydrolysis of terminal, non-reducing (2→1)-beta-D-fructofuranose residues in oligosaccharides, and more particularly to the selective hydrolysis of small fructans like 1-kestose but not sucrose by enzymes, more particularly, by 1-FEH enzymes (EC 3.2.1.153). In this way, the present invention relates to isolated polypeptides capable of hydrolyzing 1-kestose in the presence of sucrose but lacking sucrase (invertase) activity, and polynucleotides encoding the same.

BRIEF SUMMARY OF THE INVENTION

The present invention relates to an efficient, advantageous and economically viable industrial process using specific enzymes (kestose hydrolases) to enable the use of sugar mixtures (preferably derived from sugarcane, sugar beet or other crop plants with an increased storage carbohydrate content in the form of fructans) containing 1-kestose in the industrial production of sucrose (as crystallized sugar).

The present invention seeks to provide a method for conversion of 1-kestose into sucrose and fructose in a sugar solution, containing kestose and more than 10 mM sucrose (3 g/L), wherein said method comprises the enzymatic hydrolysis (preferably using 1-FEH enzymes—EC 3.2.1.153) of 1-kestose.

The present invention also seeks to provide a method of producing a polypeptide having 1-Kestose Hydrolase activity, comprising: (a) cultivating a recombinant host cell transformed with a heterologous nucleic acid construct coding for hydrolases acting on glycosidic compounds under conditions conducive for production of the polypeptide; and (b) recovering the polypeptide.

The present invention also seeks to provide a composition comprising the above polypeptide.

DETAILED DESCRIPTION OF THE INVENTION

Figure 1:
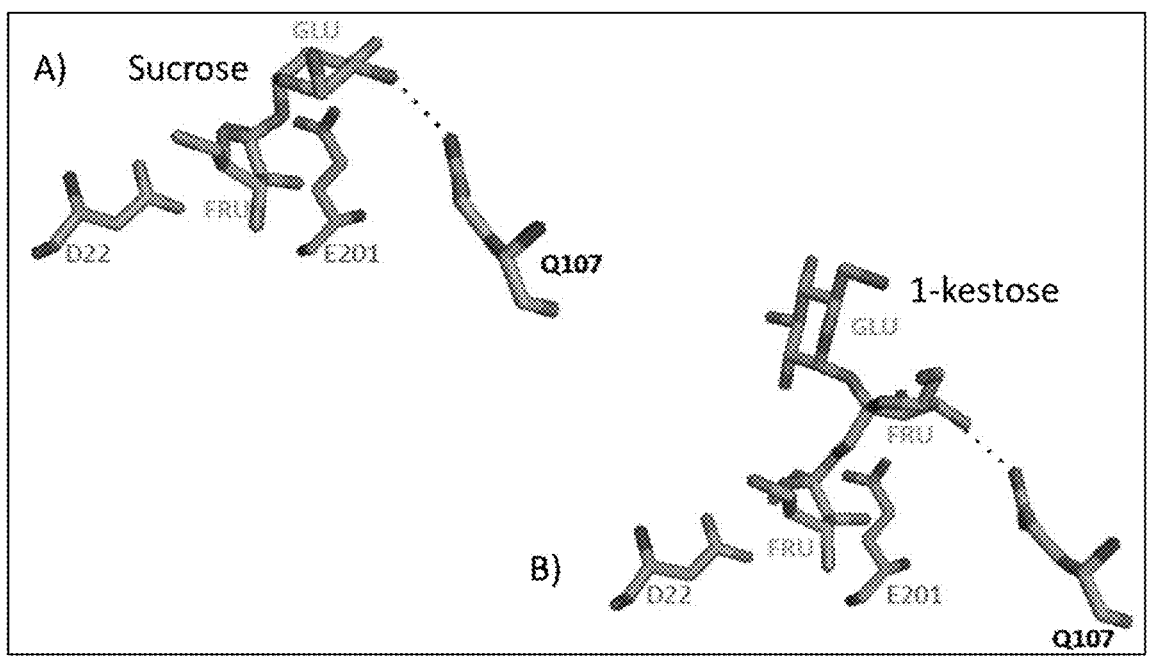
FIG. 1 is the suggested mechanism of 1-FEH inhibition by sucrose, with part A) showing Catalytic site of chicory 1-FEHIIa with sucrose as ligand (PDB: 2ADE) and part B) showing Catalytic site of chicory 1-FEHIIa with 1-kestose as ligand (PDB: 2AEZ).

One embodiment according to the present invention refers to a method of producing a polypeptide having Kestose Hydrolase activity, comprising (a) cultivating a recombinant host cell transformed with a heterologous nucleic acid construct coding for hydrolases acting on glycosidic compounds under conditions conducive for production of the polypeptide; and (b) recovering the polypeptide.

According to the method of producing a polypeptide having Kestose Hydrolase activity of the present invention the recombinant host cell is a prokaryotic or eukaryotic cell. In a preferred aspect of the present invention, said cell is a yeast cell or filamentous fungal cell. In a most preferred aspect of the present invention, said cell is a *Pichia*, a *Myceliophthora*, a *Thielavia*, a *Trichoderma*, an *Aspergillus* or a *Saccharomyces* cell.

In one aspect, the recombinant host cell of the above method is transformed by a vector comprising a polynucleotide sequence encoding at least one hydrolase acting on glycosidic compounds. In a preferred aspect, the abovementioned polynucleotide sequence encodes at least one 1-FEH enzyme (EC 3.2.1.153), wherein said 1-FEH enzyme is listed at Table 1. In another aspect, the 1-FEH enzyme is engineered to show increased performance for the conversion of 1-kestose into sucrose and fructose in the presence of sucrose (more than 10 mM).

In a further aspect, the invention relates to a composition comprising the polypeptide having Kestose Hydrolase activity according to the present invention and a stabilizer. In one embodiment, the composition comprises polypeptides having Kestose Hydrolase activity according to the present invention and polypeptides having Dextranase activity. In another embodiment, the composition comprises polypeptides having Kestose Hydrolase activity, polypeptides having Dextranase activity and polypeptides having Amylase activity.

1-FEH Inhibition by Sucrose

Among the 1-FEH enzymes characterized so far in the state of the art, the vast majority is completely inhibited by sucrose at low mM concentration (Verhaest et al. 2007; Le Roy et al. 2008). While it is not straightforward to compare enzyme inhibition data from different research groups, a few 1-FEH enzymes can be identified as "being less inhibited by sucrose": 1-FEH I from Chicory Roots (Claessens, Van Laere, and De Proft 1990), 1-FEH I from *Helianthus* (Xu et al. 2014) and (6 and 1)-FEH from *Arabidopsis thaliana* (De Coninck et al. 2005). All of them were reported to retain at least 50% of their activity in the presence of 10 mM of sucrose.

The present invention relates to fructosyl hydrolysis, particularly the hydrolysis of terminal, non-reducing (2→1)-beta-D-fructofuranose residues in oligosaccharides, and more particularly to the selective hydrolysis of small fructans like 1-kestose by 1-FEH enzymes in the presence of substantial amounts (above 10 mM) of sucrose.

In this way, one aspect of the present invention consists in a method for conversion of 1-kestose into sucrose and fructose in a sugar solution containing more than 10 mM sucrose, wherein said method comprises the enzymatic hydrolysis of 1-kestose.

Structural Determinants for Sucrose Inhibition in 1-FEH Enzymes

While consistent enzyme kinetics data is essential for an in deep understanding of substrate specificity, specific activity and inhibition profile of 1-FEH candidates, three-dimensional structures, protein alignments and molecular modeling has the potential to shed some light on the structural determinants for sucrose inhibition in 1-FEH enzymes.

As discussed by Verhaest and colleagues (2007), sucrose inhibition could be related to conserved protein regions among plant cell wall invertases and FEHs known as 'GSAT' and 'YTG'. Enzymes reported as strongly inhibited by sucrose contain a serine or a glycine residue in the YTG region while plant invertases and some FEHs that are reported as not, or only very weakly, inhibited by sucrose contain a W82 homologue (using *Cichorium intybus* 1-FEH IIa protein as reference) stacking with a hydrophobic amino acid. Interestingly, in chicory 1-FEH I, which is described as very weakly inhibited by sucrose, a leucine instead of tryptophan (W82) is observed in the GSAT region.

In general, the terminal fructosyl unit is positioned in a very similar way at the −1 subsite on proteins belonging to the family GH 32. In this orientation, the anomeric C2 of fructose (i.e., the one that will suffer the nucleophilic attack and will be covalently attached to the enzyme during hydrolysis) is correctly positioned between the two catalytic active amino acids Glutamate and Aspartate, (respectively D22 and E201 on 1-FEH IIa). Contrariwise, glucosyl unit of sucrose is found in a slightly altered position in 1-FEH IIa enzyme from *Cichorium intybus*. In this position, the active site E201 forms a short H-linkage with the O2 of the glucosyl part of sucrose, impairing its action as acid-base catalyst. Consequently, the glycosidic oxygen O1 will not be protonated and an enzymatic reaction (i.e., the nucleophilic attack and the sucrose hydrolysis) will not occur. When the substrate 1-kestose is bound in the active site, is the "second fructosyl residue" that lies in the S1 subsite and the oxygen O3 forms a close intramolecular hydrogen bond with the glycosidic oxygen O1' between glucose and fructose. In this way, the acid-base catalyst E201 can fulfil its function as proton donor to the glycosidic oxygen O1.

Verhaest and colleagues (2007) speculate that sucrose bind in the so called "inhibitor configuration" because the high conserved GH32 residue W82 is shifted further away from the active site in 1-FEH IIa enzyme, probably because it does not stack with an aromatic residue as observed in the microbial exo-inulinases enzymes. Most probably, the smaller residues such as glycine and serine at YTG region allow a different position of W82 and the binding of sucrose in the inhibitor configuration. Interestingly, all plant invertases contain a W82 homologue in the GSAT region that stacks with a hydrophobic amino acid at YTG region, which probably prevents the binding of sucrose in the inhibitor configuration.

A probable mechanism for inhibition considers the position of sucrose, compared to 1-kestose, in chicory 1-FEH IIa catalytic site (FIG. 1). This figure shows that the fructosyl moiety of 1-kestose (B) bound to 1-FEH locates roughly in the same position as the glucosyl moiety of sucrose (A). However, because of the longer binding distance between two fructosyl units compared with the binding distance between the fructosyl and glucosyl moieties in sucrose, this last sugar binds in an orientation that prevents it from hydrolysis.

Figure 2:
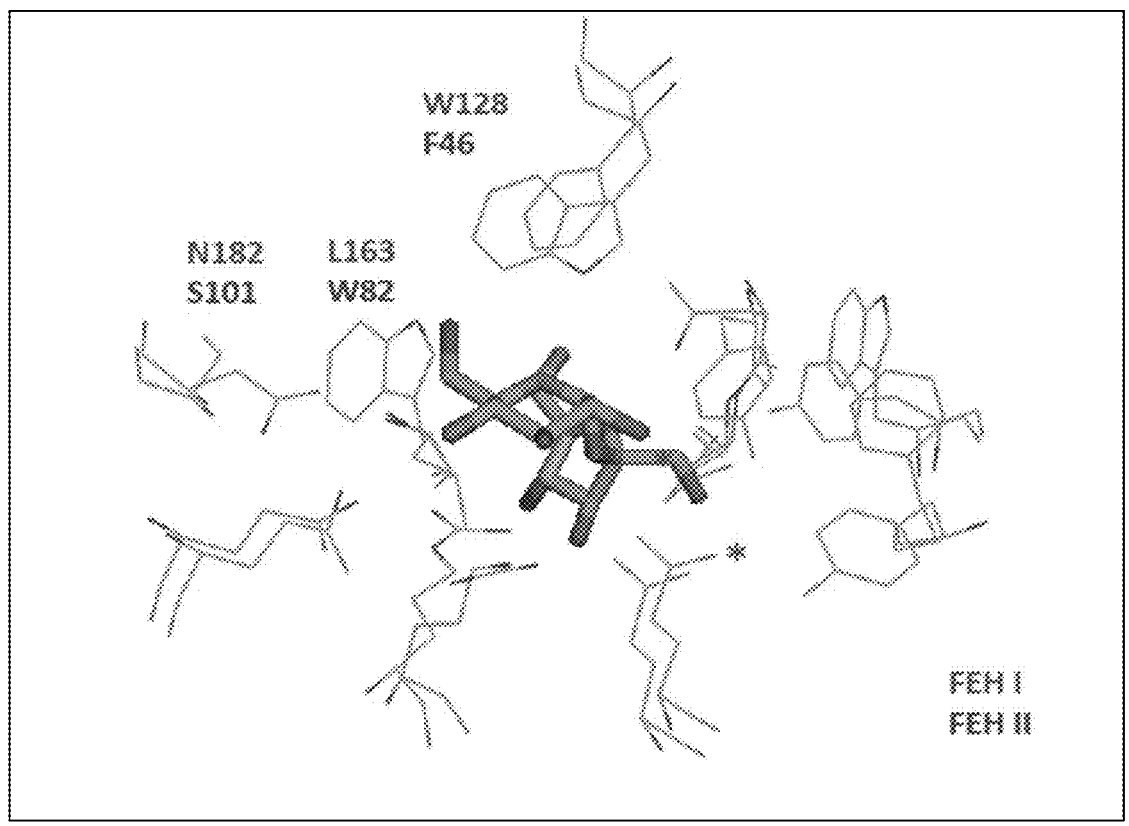
FIG. 2 is the Homology modeling of chicory (*Cichorium intybus*) 1-FEH IIa (PDB: 2ADE) and 1-FEH I complexed with sucrose (in the center) with residues highlighted in red corresponding to 1-FEH I and those highlighted in blue corresponding to 1-FEH IIa.

In order to elucidate the residues that might be responsible for sucrose binding at the catalytic site, a homology model was generated in which the crystal structure of chicory 1-FEHIIa (PDB: 2ADE) was superimposed with the chicory 1-FEHI (FIG. 2). The main differences observed were: i) the presence of a W82 residue in 1-FEHIIa, instead of the L163 homologue in 1-FEHI; ii) the presence of a S101 residue in 1-FEHIIa, instead of the N182 homologue in 1-FEHI. The tryptophan present in position 82 of 1-FEHII apparently leads to a higher interaction with glucosyl moiety of sucrose than its Leucine homologue in 1-FEHI (FIG. 2). This interaction stabilizes sucrose binding to the active site, preventing 1-kestose to enter. Residues modifications that decrease the interaction of glucosyl moiety of sucrose to the active site might decrease enzymatic inhibition by the sugar. Highlighting this view, mutagenesis experiments in the literature showed that W82L and S101L mutants of 1-FEH IIa enzyme were no longer inhibited by 10 mM sucrose, against a 63% inhibition of the wild type (Verhaest et al., 2007).

The present invention relates to fructosyl hydrolysis, particularly the hydrolysis of terminal, non-reducing (2→1)-beta-D-fructofuranose residues in oligosaccharides, and more particularly to the selective hydrolysis of small fructans like 1-kestose by native or engineered/mutated 1-FEH enzymes in the presence of sucrose. Some of the Kestose Hydrolases disclosed by the present invention, although not limiting its scope, are listed in Table 2.

TABLE 2

Kestose hydrolases for selective hydrolysis of small fructans.

| Gene | GenBank accession | GSAT Sequence | YTG Sequence |
|---|---|---|---|
| 1-FEHI [Helianthus tuberosus] | AJW31155.1 | GCFTGSST | LYTAQDA |
| 1-FEHI [Cichorium intybus] | CAC19366.1 | GCLSGSAT | ILYTCQDVN |

TABLE 2-continued

Kestose hydrolases for selective hydrolysis of small fructans.

| Gene | GenBank accession | GSAT Sequence | YTG Sequence |
|---|---|---|---|
| 1-FEH IIa WT [Cichorium intybus] | CAC37922.1 | SCWSGSAT | MLYTGSDSK |
| 1-FEH IIa (W82L) [Cichorium intybus] | | SCL*SGSAT | MLYTGSDSK |
| 1-FEH IIa (S101L) [Cichorium intybus] | | SCWSGSAT | MLYTGL*DSK |
| 1-FEH IIa (W82L/S101L) [Cichorium intybus] | | SCL*SGSAT | MLYTGL*DSK |
| 1-FEH [Campanula rapunculoides] | CAD49079.1 | SCFSGSAT | LYTCL-DT |
| 1-FEH [Brassica napus] | AFO66503.1 | SCWSGSAT | ILYTCL-EE |
| 1-FEH IIa (W82L/S101L) | | SCL*SGSAT | MLYTGL*DSK |
| 1-FEH w1 [Triticum aestivum] | CAD56806.1 | GCWTGSVT | IIYTGGDKD |
| 1-FEH w2 [Triticum aestivum] | CAD48199.1 | GCWTGSVT | IIYTGGDID |
| 1-FEH w1 [Triticum aestivum] (W84L) | | GCL*TGSVT | IIYTGGDKD |
| 1-FEH w1 [Triticum aestivum] (G103L) | | GCWTGSVT | IIYTGL*DKD |
| 1-FEH w1 [Triticum aestivum] (W84L/G103L) | | GCL*TGSVT | IIYTGL*DKD |
| 1-FEH w2 [Triticum aestivum] (W84L) | | GCL*TGSVT | IIYTGGDID |
| 1-FEH w2 [Triticum aestivum] (G103L) | | GCWTGSVT | IIYTGL*DID |
| 1-FEH w2 [Triticum aestivum] (W84L/G103L) | | GCL*TGSVT | IIYTGL*DID |
| (6 and 1)-FEH [Arabidopsis thaliana] | AAL31183.1 | SCWSGSAT | ILYTCL-DVN |

*aminoacid substitution

Process: The Use of the Enzyme for Higher Yield Sugar Production

In a particular embodiment according to the present invention, an enzyme having Kestose Hydrolase activity is intended for use in the sugar industry for conversion of 1-kestose into sucrose, in various sugar solutions. The term "Kestose hydrolase" means enzymes capable of performing the hydrolysis of 1-kestose into sucrose and fructose in the presence of substantial amounts (above 10 mM) of sucrose.

The Kestose Hydrolase enzyme used herein may be produced by any means known in the art.

In one aspect, the invention relates to the application of an enzyme having Kestose Hydrolase activity of the invention for conversion of 1-kestose into sucrose and fructose in a sugar solution.

In a further aspect, the invention relates to a method for conversion of 1-kestose into sucrose and fructose in a sugar solution comprising contacting the sugar solution with an enzyme having Kestose Hydrolase activity according to the invention. In particular, the enzyme having Kestose Hydrolase activity is a 1-FEH enzyme (EC 3.2.1.153).

In a preferred aspect of the present invention, the 1-FEH enzyme shows increased performance for the conversion of 1-kestose into sucrose and fructose in the presence of sucrose (more than 10 mM). Table 3 demonstrates a comparison of sucrose inhibition profiles for some of the Kestose Hydrolases disclosed by the present invention.

In particular, the sugar solution is selected from the group comprising any juice (including primary juice, secondary juice, mixed juice, sulphited juice, limed juice, decanted juice, filtered juice, evaporated juice, concentrated juice, or juices derived from unit operations of sugarcane mills, beet sugar mills or sugar refinery), any syrup (concentrated syrup, sulphited sugar, floated syrup, limed syrup, syrup derived from unit operation of sugarcane mills, sugar beet industry or sugar refinery), any massacuite (massacuite A, massacuite B, massacuite C), any molasses, any magma, raw sugar solution, and/or VVHP/VHP sugar solution, also affinated sugar, melted sugar, clarified sugar, carbonated sugar, phosphated sugar, (including any sugar solution derived from unit operation of sugar refinery).

The Kestose Hydrolase may be added at any suitable step during the raw sugar, white sugar or refined sugar process. In particular, the Kestose Hydrolase may be added to the sugar cane juice before or during clarification. Other suitable points to add Kestose Hydrolase could be to the holding sugar juice tanks or to syrup tanks. In another particular

TABLE 3

Sucrose inhibition profiles for some of the Kestose hydrolases

| Gene | GSAT Sequence | YTG Sequence | Sucrose inhibition | % inhibition by sucrose | Reference |
| --- | --- | --- | --- | --- | --- |
| 1-FEHI [Helianthus tuberosus] | GC*TGSST | LYTAQDA | Weak | 13% with 10 mM sucrose 49% with 100 mM sucrose | (Xu et al. 2014) |
| 1-FEHI [Cichorium intybus] | GC*SGSAT | ILYTGQDVN | Weak | 25% with 20 mM sucrose | (Claessens et al. 1990; Verhaest et al. 2007) |
| 1-FEH IIa [Cichorium intybus] | SCWSGSAT | MLYTGSDSK | Strong | 63% with 10 mM sucrose | (Verhaest et al. 2007) |
| 1-FEH IIa (W82L) [Cichorium intybus] | SCL*SGSAT | MLYTGSDSK | Weak | 0% with 10 mM sucrose | (Verhaest etal. 2007) |
| 1-FEH IIa (S101L) [Cichorium intybus] | SCWSGSAT | MLYTGL*DSK | Weak | 0% with 10 mM sucrose | (Verhaest et al. 2007) |
| 1-FEH w1 [Triticum aestivum] | GCWTGSVT | IIYTCGDKD | Strong | 50% with 1 mM sucrose | (Van Den Ende et al. 2003) |
| 1-FEH w2 [Triticum aestivum] | GCWTGSVT | IIYTCGDID | Strong | 50% with 1 mM sucrose | (Van Den Ende et al. 2003) |

*aminoacid substitution

Alternatively, the 1-FEH enzyme is engineered to show increased performance for the conversion of 1-kestose into sucrose and fructose in the presence of sucrose (more than 10 mM).

In the present context, the contact of the Kestose Hydrolase enzyme with the sugar solution may be performed by any means known in the art.

In the present context a "sugar solution" means any solution comprising sugar derived from sugarcane, sugar beet or other crop plants with an increased storage carbohydrate content in the form of fructans, particularly 1-kestose.

embodiment the Kestose Hydrolase is added during the evaporation step, e.g., to the molasses stream between evaporators, more particularly prior to the last evaporator.

The Kestose Hydrolase may be also used in a composition with polypeptides having dextranase activity and polypeptides having amylase activity, since dextran and starch are common contaminants in sugar production processes.

Example—Results

As a proof-of-concept, four kestose hydrolase targets were selected, cloned, expressed in *Pichia pastoris* and tested for hydrolysis of 1-kestose to sucrose and fructose, in the presence of sucrose. The targets, depicted in Table 4, comprise one wild type 1-FEH from *Campanula rapuncu-* loides, mutated versions of 1-FEH w1 and w1 from *Triticum aestivum* and a mutated version of 1-FEH IIa from *Cichorium intybus*.

Figure 3:
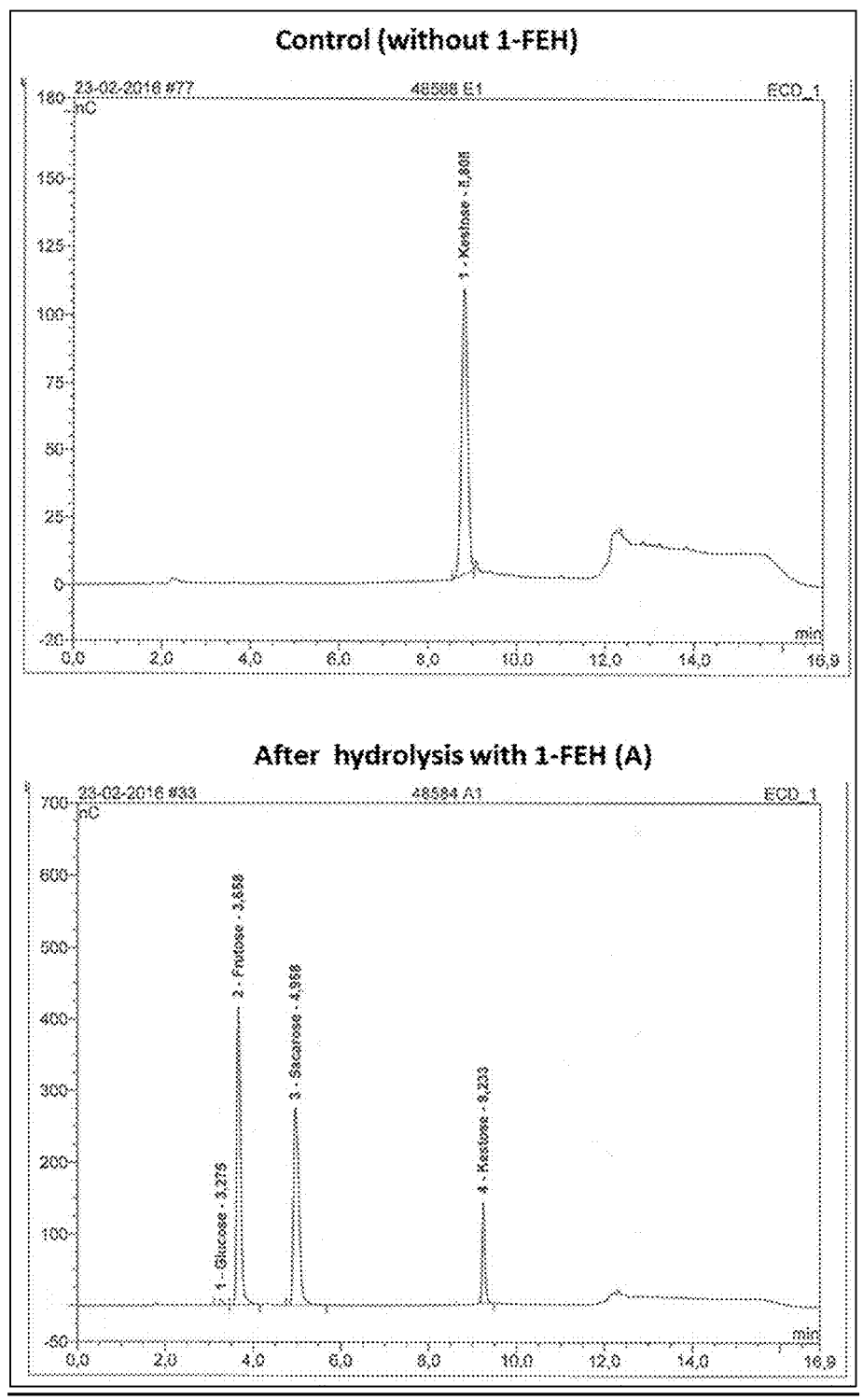
FIG. 3 are HPAEC-PAD Dionex Chromatograms illustrating the validation of 1-kestose hydrolysis by 1-FEH enzyme A (*Campanula rapunculoides*). The remaining target enzymes tested showed a similar reaction product pattern, with only fructose and sucrose being produced. The upper panel of FIG. 3 indicates the chromatogram of control reaction containing the substrate 1-kestose without enzyme and the lower panel of FIG. 3 shows the formation of fructose and sucrose after hydrolysis of 1-kestose by 1-FEH A, at the concentration of 0.75 mg/mL, for 1 hour, at 30° C. Initial concentration of 1-kestose was 10 mM in all experiments.

Targets B, C and D from Table 4 are described in the literature as strongly inhibited by sucrose (Verhaest et al. 2007; Van Den Ende et al. 2003). In order to obtain enzymes able to hydrolyze 1-kestose in the presence of high amounts of sucrose (e.g. 380 mM) point mutations were performed to substitute W82 homologue Tryptophan residue present within the GSAT region for a Leucine residue. These substitutions are supposed to decrease the interaction of glucosyl moiety of sucrose to the active site of the enzymes, leading to destabilization of sucrose binding and, consequently, less inhibition.

fixed and increasing concentrations of sucrose were added to the reaction. Inhibition percentage was calculated by the amount of fructose released in each reaction, compared to the fructose released in the reaction without added sucrose (FIG. 3).

The 1-FEH enzyme from *Campanula rapunculoides* (line A in Table 4) was selected as a potential target because of its natural substitution of the W82 homologue in the GSAT region by a phenylalanine residue (Table 4). One could expect a low inhibition profile by sucrose, but our data shows that the enzyme is more than 70% inhibited in the presence of 100 mM sucrose. This probably happens because phenylalanine has a similar role as tryptophan in interacting to the glucosyl moiety of sucrose in the active

TABLE 4

Kestose hydrolase targets tested for kestose hydrolase activity and sucrose inhibition.

| ID | Gene | Source Organism | GenBank accession (WT version) | GSAT region | YTG region | % Inhibition of WT enzyme by Sucrose |
|---|---|---|---|---|---|---|
| A | 1-FEH (Wild Type) | *Campanula rapunculoides* | CAD49079.1 | SC$^F$SGSAT | LYTG$^L$DT | — |
| B | 1-FEH w1 (W135L) | *Triticum aestivum* | CAD56806.1 | GC$^L$TGSVT | IIYTC$^G$DKD | 50% with 1 mM sucrose |
| C | 1-FEH w2 (W134L) | *Triticum aestivum* | CAD48199.1 | GC$^L$TGSVT | IIYTC$^G$DID | 50% with 1 mM sucrose |
| D | 1-FEH IIa (W120L) | *Cichorium intybus* | CAC37922.1 | SC$^L$SGSAT | MLYTC$^S$DSK | 63% with 10 mM sucrose |

*aminoacid substitution

The enzymes A, B, C and D were expressed in *Pichia pastoris* KM71H strain with a fusion GFP protein at C-terminal in 300 mL of culture media. After 48-hour induction with 0.5% (v/v) mM of methanol, the recombinant proteins were partially purified by precipitation with ammonium sulphate at 70% of saturation, followed by solubilization with sodium phosphate buffer 50 mM pH6.0. The partially purified proteins were concentrated and analyzed by SDS-PAGE and blue-light transluminator for GFP fluorescence. The enzymatic activity assays of the partially purified enzymes were evaluated using 10 mM 1-kestose as substrate, 50 uL of enzyme and sucrose as inhibitor ranging from zero to 380 mM, in a 100 μL-reaction buffered with sodium phosphate 50 mM pH6.0. The reactions were carried for 1 hour at 30° C. and stopped by heating at 95° C. for 5 minutes. The reactions were than diluted to 4 mL with ultrapure water and analyzed high-pressure anion-exchange chromatography with pulsed amperometric detection (HPAEC-PAD, Dionex, Sunnyvale, Calif., USA). Enzyme relative activity was determined by the amount of fructose released.

HPAEC-PAD analysis showed that all enzymes tested are kestose hydrolases without sucrase activity, since the only reaction products were fructose and sucrose, but no glucose was detected. An example of such HPAEC-PAD chromatograms can be seen in FIG. 3.

After identifying that the chosen targets are active against 1-kestose but not sucrose, we performed sucrose inhibition studies in which the amount of enzyme and substrate were site of the enzyme. This is reasonable, since both amino acids have aromatic side-chains.

Figure 4:
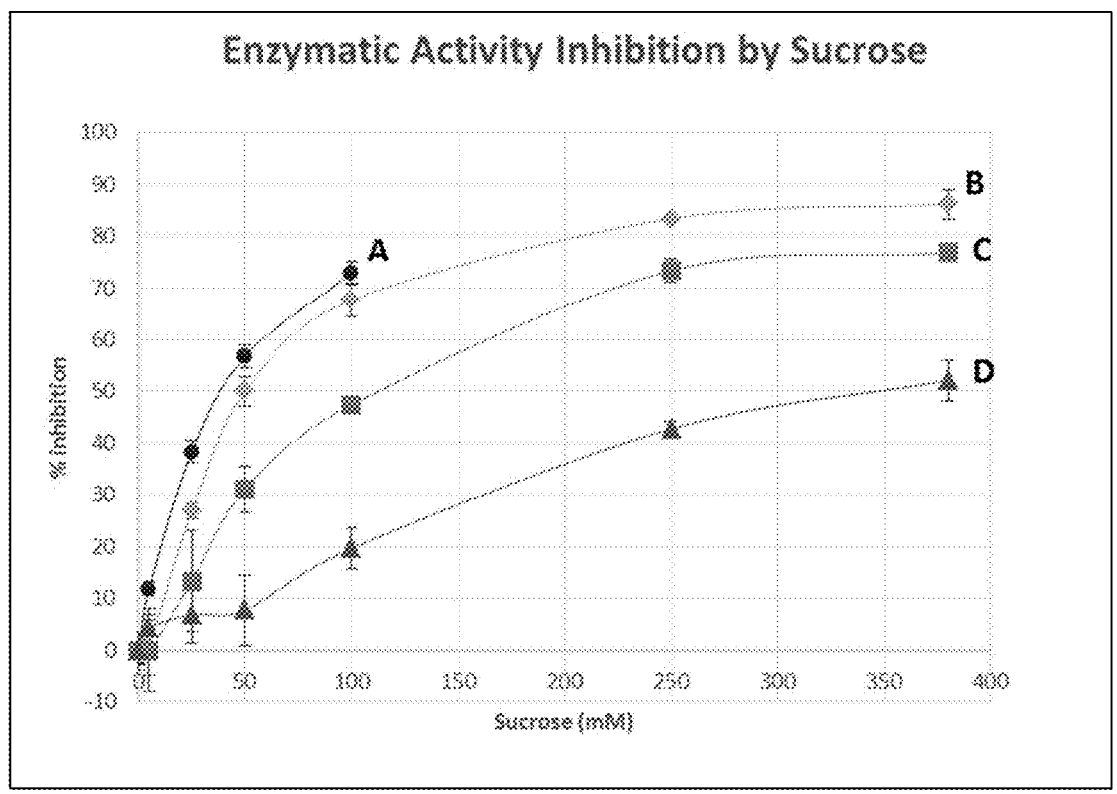
FIG. 4 shows the Sucrose inhibition assay of four 1-FEH targets, with the Target ID letters corresponding to Table 4.

The *Triticum aestivum* enzymes 1-FEH w1 and 1-FEH w2 (lines B and C, respectively in FIG. 4) were point-mutated to substitute the W82 homologue of GSAT region for a leucine residue, generating the (W135L) and (W134L) versions, respectively (Table 4). These mutations were expected to cause a decrease in the interaction of sucrose to the active site, preventing inhibition. However, as seen in FIG. 4, the enzyme B had a similar inhibition pattern of enzyme A and the enzyme C showed a lower inhibition, but higher than 75% at 380 mM of sucrose. These results are probably explained by the presence of a threonine residue adjacent to the leucine substitution (Table 4), that may also be interacting and stabilizing sucrose in the active site. Thus, further point mutations in these threonine residues have a high potential to decrease enzyme inhibition by sucrose.

The target enzyme 1-FEH IIa from *Cichorium intybus* is described as strongly inhibited by sucrose (Verhaest et al. 2007). The same authors showed that the substitution of the W82 homologue residue of GSAT region by a leucine (W120L version, Table 4) decreased enzymatic inhibition from 63% to 0% in the presence of 10 mM sucrose. Since sucrose concentrations usually reach 380 mM in the industrial processes from sugarcane, inhibition data of kestose hydrolases in such sucrose concentrations are necessary. In this sense, the same W120L mutation of 1-FEH IIa from *Cichorium intybus* was tested and the inhibition reached 52% at 380 mM sucrose (line D in FIG. 4). These results are representative examples of using this enzyme for industrial application for conversion of 1-kestose into sucrose and fructose. Other mutations may have additional effects, like the S139L substitution, which was also demonstrated by Verhaest et al., 2007 to reduce sucrose inhibition in the same enzyme. The double mutation (W120L and S139L) has also a high potential to decrease inhibition in high sucrose concentrations (e.g. 380 Mm).

Full Citations for Non-Patent Literature Cited within:

Claessens, Guy, André Van Laere, and Maurice De Proft. 1990. "Purification and Properties of an Inulinase from Chicory Roots (*Cichorium Intybus* L.)." Journal of Plant Physiology 136 (1): 35-39. doi:10.1016/S0176-1617(11) 81611-1.

De Coninck, Barbara, Katrien Le Roy, Isolde Francis, Stefan Clerens, Rudy Vergauwen, Aileen M. Halliday, Steven M. Smith, André Van Laere, and Wim Van Den Ende. 2005. "*Arabidopsis* AtcwINV3 and 6 Are Not Invertases but Are Fructan Exohydrolases (FEHs) with Different Substrate Specif WO96/01904, WO96/21023, WO98/39460, WO99/24593, WO2006066969 and WO2009152285icities." Plant, Cell and Environment 28 (4): 432-43. doi:10.1111/j.1365-3040.2004.01281.x.

Le Roy, Katrien, Willem Lammens, André Van Laere, and Wim Van Den Ende. 2008. "Influencing the Binding Configuration of Sucrose in the Active Sites of Chicory Fructan 1-Exohydrolase and Sugar Beet Fructan 6-Exohydrolase." New Phytologist 178 (November 2015): 572-80. doi:10.1111/j.1469-8137.2008.02386.x.

Sainz-Polo, M. A., M. Ramirez-Escudero, A. Lafraya, B. Gonzalez, J. Marin-Navarro, J. Polaina, and J. Sanz-Aparicio. 2013. "Three-Dimensional Structure of *Saccharomyces* Invertase: ROLE OF A NON-CATALYTIC DOMAIN IN OLIGOMERIZATION AND SUBSTRATE SPECIFICITY." Journal of Biological Chemistry 288 (14): 9755-66. doi:10.1074/jbc.M112.446435.

Van Den Ende, Wim, Stefan Clerens, Rudy Vergauwen, Liesbet Van Riet, André Van Laere, Midori Yoshida, and Akira Kawakami. 2003. "Fructan 1-Exohydrolases. Beta-(2,1)-Trimmers during Graminan Biosynthesis in Stems of Wheat? Purification, Characterization, Mass Mapping, and Cloning of Two Fructan 1-Exohydrolase Isoforms." Plant Physiology 131 (2): 621-31. doi:10.1104/pp.015305.

Verhaest, Maureen, Willem Lammens, Katrien Le Roy, Camiel J. De Ranter, André Van Laere, Anja Rabijns, and Wim Van Den Ende. 2007. "Insights into the Fine Architecture of the Active Site of Chicory Fructan 1-Exohydrolase: 1-Kestose as Substrate vs Sucrose as Inhibitor." New Phytologist 174 (1): 90-100. doi:10.1111/j.1469-8137.2007.01988.x.

Xu, Huanhuan, Mingxiang Liang, Li Xu, Hui Li, Xi Zhang, Jian Kang, Qingxin Zhao, and Haiyan Zhao. 2014. "Cloning and Functional Characterization of Two Abiotic Stress-Responsive Jerusalem Artichoke (*Helianthus tuberosus*) Fructan 1-Exohydrolases (1-FEHs)." Plant Molecular Biology 87 (1-2): 81-98. doi:10.1007/s11103-014-0262-1.

What is claimed is:

1. A method of improving sucrose crystal recovery, the method comprising contacting a sugar solution comprising kestose and more than 100 mM sucrose (30 g/L) with an enzyme having kestose hydrolase activity,
wherein the enzyme having kestose hydrolase activity has an amino acid sequence selected from the group consisting of SEQ ID NO. 5 and SEQ ID NO. 7; and
wherein the sugar solution is derived from sugarcane, sugar beets, and combinations thereof.

2. The method according to claim 1, further comprising the addition of polypeptides having dextranase activity.

3. The method according to claim 1, further comprising the addition of polypeptides having amylase activity.

4. The method according to claim 2, further comprising the addition of polypeptides having amylase activity.

5. The method according to claim 1, wherein the 1-FEH enzyme is a recombinant polypeptide produced by a method comprising:
   a) cultivating a recombinant host cell transformed with a heterologous nucleic acid construct encoding at least one hydrolase acting on glycosidic compounds under conditions conducive for production of polypeptides; and
   b) recovering the polypeptides.

6. The method according to claim 1, wherein the sugar solution comprises sucrose in a range from 100 mM to 380 mM and kestose.

7. The method according to claim 5, wherein the heterologous nucleic acid construct of step (a) comprises a nucleotide sequence selected from the group consisting of SEQ ID NO. 6 and SEQ ID NO. 8.

* * * * *

SEQUENCE LISTING

```
<160> NUMBER OF SEQ ID NOS: 12

<210> SEQ ID NO 1
<211> LENGTH: 538
<212> TYPE: PRT
<213> ORGANISM: Campanula rapunculoides

<400> SEQUENCE: 1

Ser Asp Gln Pro Tyr Arg Thr Gly Tyr His Phe Gln Pro Pro Gln Asn
1               5                   10                  15

Trp Met Asn Asp Pro Asn Gly Pro Met Tyr Tyr Lys Gly Val Tyr His
            20                  25                  30

Phe Phe Tyr Gln Tyr Asn Pro Asn Gly Pro Leu Phe Gly Asp Ile Met
        35                  40                  45

Ile Trp Gly His Ser Val Ser Tyr Asp Leu Val Asn Trp Ile His Ile
    50                  55                  60

Asp Pro Ala Ile Tyr Pro Thr Asp Pro Ala Asp Ile Asn Ser Cys Phe
65                  70                  75                  80

Ser Gly Ser Ala Thr Phe Leu Pro Gly Tyr Lys Pro Val Met Leu Tyr
                85                  90                  95

Thr Gly Leu Asp Thr Glu Lys Arg Gln Val Gln Asn Leu Ala Val Pro
            100                 105                 110

Lys Asn Leu Ser Asp Pro Phe Leu Arg Glu Trp Val Lys His Lys Ala
        115                 120                 125

Asn Pro Ile Met Thr Thr Pro Glu Gly Val Lys Ala Asp Asp Phe Arg
    130                 135                 140

Asp Pro Ser Thr Ala Trp Leu Gly Tyr Asp Gly Lys Trp Arg Val Leu
145                 150                 155                 160

Val Gly Ser Lys Lys Asn Asp Leu Gly Val Ala Tyr Leu Tyr Gln Ser
                165                 170                 175
```

| Lys | Asp | Phe | Val | Lys | Trp | Glu | Arg | Phe | Asp | Tyr | Pro | Leu | Met | Ser | Met |
|     |     |     | 180 |     |     |     | 185 |     |     |     | 190 |     |     |     |     |

| Met | Glu | Thr | Ser | Thr | Trp | Glu | Cys | Pro | Asp | Phe | Phe | Pro | Val | Ser | Val |
|     | 195 |     |     |     |     | 200 |     |     |     |     | 205 |     |     |     |     |

| Ser | Ser | Thr | Asn | Gly | Leu | Asp | Thr | Ser | Gly | Val | Ile | Asn | Pro | Gly | Val |
| 210 |     |     |     |     | 215 |     |     |     |     | 220 |     |     |     |     |     |

| Lys | His | Val | Val | Lys | Val | Gly | Phe | Asn | Gly | Ile | Asp | Trp | Tyr | Thr | Ile |
| 225 |     |     |     |     | 230 |     |     |     |     | 235 |     |     |     |     | 240 |

| Gly | Thr | Leu | Ser | Glu | Arg | Asp | Asn | Tyr | Val | Pro | Glu | Asn | Gly | Leu | Lys |
|     |     |     |     | 245 |     |     |     |     | 250 |     |     |     |     | 255 |     |

| Gly | Asn | Ser | Leu | Asp | Met | Arg | Tyr | Asp | Tyr | Gly | Lys | Phe | Tyr | Ala | Ser |
|     |     |     | 260 |     |     |     |     | 265 |     |     |     |     | 270 |     |     |

| Lys | Ser | Phe | Tyr | Asp | Asn | Ala | Lys | Gln | Arg | Arg | Val | Leu | Trp | Gly | Trp |
|     |     | 275 |     |     |     |     | 280 |     |     |     |     | 285 |     |     |     |

| Ile | Ser | Glu | Ala | Asp | Ala | Gln | Glu | Asp | Val | Ala | Arg | Gly | Trp | Ser |     |
|     | 290 |     |     |     |     | 295 |     |     |     |     | 300 |     |     |     |     |

| Gly | Leu | Gln | Ala | Val | Pro | Arg | Ser | Val | Trp | Leu | Asp | Arg | Asn | Gly | Lys |
| 305 |     |     |     |     | 310 |     |     |     |     | 315 |     |     |     |     | 320 |

| Gln | Leu | Val | Gln | Trp | Pro | Val | Glu | Glu | Ile | Glu | Lys | Leu | Arg | Glu | Asn |
|     |     |     |     | 325 |     |     |     |     | 330 |     |     |     |     | 335 |     |

| Glu | Val | Lys | Phe | Ser | Asn | Lys | Glu | Leu | Glu | Gly | Gly | Ser | Leu | Phe | Glu |
|     |     |     | 340 |     |     |     |     | 345 |     |     |     |     | 350 |     |     |

| Val | Glu | Gly | Ile | Thr | Ala | Ser | Gln | Ala | Asp | Val | Lys | Ile | Ser | Phe | Lys |
|     |     | 355 |     |     |     |     | 360 |     |     |     |     | 365 |     |     |     |

| Leu | Ser | Asn | Leu | Glu | Glu | Ala | Glu | Glu | Leu | Asp | Pro | Ser | Trp | Thr | Asp |
| 370 |     |     |     |     | 375 |     |     |     |     | 380 |     |     |     |     |     |

| Pro | Gln | Leu | Leu | Cys | Ser | Glu | Met | Gly | Val | Ser | Ser | Lys | Gly | Lys | Tyr |
| 385 |     |     |     |     | 390 |     |     |     |     | 395 |     |     |     |     | 400 |

| Gly | Pro | Phe | Gly | Leu | Leu | Ala | Leu | Ala | Ser | Asp | Asp | Leu | Thr | Glu | Gln |
|     |     |     |     | 405 |     |     |     |     | 410 |     |     |     |     | 415 |     |

| Thr | Ala | Ile | Phe | Phe | Arg | Val | Phe | Ser | Ser | His | Gly | Lys | Tyr | Val | Val |
|     |     |     |     | 420 |     |     |     |     | 425 |     |     |     |     | 430 |     |

| Leu | Met | Cys | Ser | Asp | Gln | Arg | Arg | Ser | Ser | Ile | Ser | Asn | Asn | Val | Glu |
|     |     |     | 435 |     |     |     |     | 440 |     |     |     |     | 445 |     |     |

| Lys | Thr | Thr | Tyr | Gly | Thr | Phe | Val | Asp | Ile | Asp | Pro | Lys | His | Glu | Glu |
|     | 450 |     |     |     |     | 455 |     |     |     |     | 460 |     |     |     |     |

| Ile | Ser | Leu | Arg | Ser | Leu | Ile | Asp | His | Ser | Ile | Ile | Glu | Ser | Phe | Gly |
| 465 |     |     |     |     | 470 |     |     |     |     | 475 |     |     |     |     | 480 |

| Ala | Glu | Gly | Lys | Ser | Cys | Ile | Thr | Ala | Arg | Val | Tyr | Pro | Arg | Leu | Ala |
|     |     |     |     | 485 |     |     |     |     | 490 |     |     |     |     | 495 |     |

| Ile | Asn | Lys | Asp | Ala | His | Leu | Tyr | Thr | Phe | Asn | Tyr | Gly | Ser | Glu | Ser |
|     |     |     | 500 |     |     |     |     | 505 |     |     |     |     | 510 |     |     |

| Val | Met | Ile | Ser | Glu | Leu | Asn | Ala | Trp | Ser | Met | Lys | Asn | Ala | His | Met |
|     |     |     | 515 |     |     |     |     | 520 |     |     |     |     | 525 |     |     |

| Ile | Val | Asp | Glu | Thr | Leu | Ser | Ser | Ala | Ala |
|     |     |     | 530 |     |     |     |     | 535 |     |

<210> SEQ ID NO 2
<211> LENGTH: 1617
<212> TYPE: DNA
<213> ORGANISM: Campanula rapunculoides

<400> SEQUENCE: 2
tctgatcaac catacagaac tggttatcat tttcaaccac ctcagaactg gatgaatgac     60

-continued

```
ccaaacggtc ctatgtacta agggagtt taccactttt tctaccagta aacccaaat     120
ggacctttgt tcggagatat tatgatctgg ggtcattcag ttagttacga tcttgtcaac    180
tggattcaca tcgaccctgc tatctaccca acagatcctg ccgacatcaa ttcttgtttt    240
tctggttccg ctactttctt gccaggatac aaacctgtta tgttgtatac cggtcttgat    300
acagaaaaga gacaagttca gaacttggct gtcccaaaga acttgtctga cccttttctt    360
agagaatggg ttaagcataa agctaaccca attatgacta cccctgaggg agtcaaggca    420
gatgacttca gagatccatc cactgcctgg ttgggttacg acggaaaatg agagttctt     480
gtcggttcaa agaaaaatga tttgggagtt gcttaccttt accagagtaa ggatttcgtc    540
aaatgggaga gattcgacta tcctttgatg tctatgatgg aaacctccac atgggagtgc    600
ccagatttct ttcctgtttc tgtctcttcc actaacggat tggacacctc cggtgttatt    660
aatccaggag tcaagcacgt tgtcaaagtt ggttttaacg gaattgattg gtacactatc    720
ggtaccttgt ccgaaagaga caattatgtt cctgagaacg gtttgaaggg aaattcactt    780
gatatgagat acgactacgg taaattctac gcatcaaaga gtttctacga taacgctaag    840
caaagaaagg ttttgtgggg atggatttct gaagcagacg ctcaagagga tgacgtcgcc    900
agaggttggt ctggattgca ggcagttcca agatccgtct ggttggatag aaatggtaaa    960
caacttgttc agtggcctgt cgaagagatt gaaaagttga gagaaaacga ggttaagttt    1020
tcaaacaagg aattggaggg tggaagtctt ttcgaagttg agggaattac tgcttcacaa    1080
gccgatgtca agatctcttt caaattgtcc aatcttgaag aggctgaaga gttggatcca    1140
tcatggaccg accctcagtt gctttgtagt gaaatgggtg tttcaagtaa aggtaaatac    1200
ggaccatttg gtttgcttgc cttggcatcc gatgacctta cagagcaaac tgctattttc    1260
tttagagttt tctcttccca tggtaaatac gttgtcttga tgtgctctga tcagagaaga    1320
tcaagtatct ccaacaacgt tgaaaagaca acttacggaa ctttcgtcga tatcgaccca    1380
aaacatgaag agatttcatt gagaagtctt atcgatcact caattatcga agtttcgga    1440
gctgagggta atcttgtat taccgccaga gtttatccta gattggcaat caacaaagac    1500
gctcatcttt acactttaa ctacggttct gaatccgtta tgatttcaga gttgaacgcc    1560
tggagtatga aaaatgcaca catgatcgtt gatgaaactt tgtcttccgc tgcctaa       1617
```

<210> SEQ ID NO 3
<211> LENGTH: 597
<212> TYPE: PRT
<213> ORGANISM: Artificial Sequence
<220> FEATURE:
<223> OTHER INFORMATION: Fructan 1-exohydrolase precursor (W135L)

<400> SEQUENCE: 3

```
Met Ala Gln Ala Trp Ala Phe Leu Leu Pro Val Leu Phe Gly Ser
1               5                   10                  15

Tyr Val Thr Ser Leu Phe Phe Pro Ser Tyr Ile Ser Gly Pro Leu Cys
            20                  25                  30

Gly Gly Asp Gly Gly Gly Arg Ser Leu Phe Leu Cys Ala Gln Ala Pro
        35                  40                  45

Lys Asp Gln Asp Pro Ser Pro Ala Val Ser Thr Met Tyr Lys Thr Ala
    50                  55                  60

Phe His Phe Gln Pro Ala Lys Asn Trp Met Asn Asp Pro Ser Gly Pro
65                  70                  75                  80

Met Tyr Phe Asn Gly Phe Tyr His Glu Phe Tyr Gln Tyr Asn Leu Asn
```

```
                        85                  90                  95
Gly Pro Ile Phe Gly Asp Ile Val Trp Gly His Ser Val Ser Thr Asp
                100                 105                 110

Leu Val Asn Trp Ile Gly Leu Glu Pro Ala Leu Val Arg Asp Thr Pro
            115                 120                 125

Ser Asp Ile Asp Gly Cys Leu Thr Gly Ser Val Thr Ile Leu Pro Gly
        130                 135                 140

Gly Lys Pro Val Ile Ile Tyr Thr Gly Gly Asp Lys Asp Gln His Gln
145                 150                 155                 160

Ala Gln Asn Ile Ala Phe Pro Lys Asn Arg Ser Asp Pro Tyr Leu Arg
                165                 170                 175

Glu Trp Ile Lys Ala Ala Asn Asn Pro Val Leu Arg Pro Asp Glu Pro
            180                 185                 190

Gly Met Asn Ser Ile Glu Phe Arg Asp Pro Thr Thr Gly Trp Ile Gly
        195                 200                 205

Pro Asp Gly Leu Trp Arg Met Ala Val Gly Gly Glu Leu Asn Gly Tyr
    210                 215                 220

Ser Ala Ala Leu Leu Tyr Lys Ser Glu Asp Phe Leu Asn Trp Thr Lys
225                 230                 235                 240

Val Asp His Pro Leu Tyr Ser His Asn Gly Ser Asn Met Trp Glu Cys
                245                 250                 255

Pro Asp Phe Phe Ala Val Leu Pro Gly Asn Asn Ala Gly Leu Asp Leu
            260                 265                 270

Ser Ala Ala Ile Pro Gln Gly Ala Lys His Ala Leu Lys Met Ser Val
        275                 280                 285

Asp Ser Val Asp Lys Tyr Met Ile Gly Val Tyr Asp Leu Gln Arg Asp
    290                 295                 300

Ala Phe Val Pro Asp Asn Val Val Asp Arg Arg Leu Trp Leu Arg
305                 310                 315                 320

Ile Asp Tyr Gly Thr Phe Tyr Ala Ser Lys Ser Phe Phe Asp Ser Asn
                325                 330                 335

Lys Asn Arg Arg Ile Ile Trp Gly Trp Ser Arg Glu Thr Asp Ser Pro
            340                 345                 350

Ser Asp Asp Leu Glu Lys Gly Trp Ala Gly Leu His Thr Ile Pro Arg
        355                 360                 365

Thr Ile Trp Leu Ala Asp Asn Gly Lys Gln Leu Leu Gln Trp Pro Val
    370                 375                 380

Glu Glu Ile Glu Ser Leu Arg Thr Asn Glu Ile Ser His Gln Gly Ile
385                 390                 395                 400

Glu Leu Asn Lys Gly Asp Leu Phe Glu Ile Lys Glu Val Asp Ala Phe
                405                 410                 415

Gln Ala Asp Val Glu Ile Gly Phe Glu Leu Ala Ser Ile Asp Asp Ala
            420                 425                 430

Asp Pro Phe Asp Pro Ser Trp Leu Leu Asp Pro Glu Lys His Cys Gly
        435                 440                 445

Glu Ala Gly Ala Ser Val Pro Gly Gly Ile Gly Pro Phe Gly Leu Val
    450                 455                 460

Ile Leu Ala Ser Asp Asn Met Asp Glu His Thr Glu Val Tyr Phe Arg
465                 470                 475                 480

Val Tyr Lys Ser Gln Glu Lys Tyr Met Val Leu Met Cys Ser Asp Leu
                485                 490                 495

Arg Arg Ser Ser Leu Arg Pro Asp Leu Glu Lys Pro Ala Tyr Gly Gly
            500                 505                 510
```

```
Phe Phe Glu Phe Asp Leu Glu Lys Glu Arg Lys Ile Ser Leu Arg Thr
            515                 520                 525

Leu Ile Asp Arg Ser Ala Val Glu Ser Phe Gly Gly Gly Arg Val
        530                 535                 540

Cys Ile Thr Ser Arg Val Tyr Pro Ala Val Leu Ala Asp Val Gly Arg
545                 550                 555                 560

Ala His Ile Tyr Ala Phe Asn Asn Gly Ser Ala Thr Val Arg Val Pro
                565                 570                 575

Gln Leu Ser Ala Trp Thr Met Arg Lys Ala Gln Val Asn Val Glu Lys
            580                 585                 590

Gly Trp Ser Ala Ile
        595

<210> SEQ ID NO 4
<211> LENGTH: 1638
<212> TYPE: DNA
<213> ORGANISM: Artificial Sequence
<220> FEATURE:
<223> OTHER INFORMATION: Fructan 1-exohydrolase precursor (W135L)

<400> SEQUENCE: 4
gatccatctc ctgctgtttc tactatgtac aagactgctt tcatttcca accagctaaa       60 aactggatga atgatccatc tggtcctatg tacttcaacg gtttctacca tgaattctac     120
caatacaact tgaacggtcc tatcttcgga gatattgttt ggggtcactc tgtttctact     180
gatttggtta attggattgg tttggagcca gctttggtta gagatactcc ttctgatatt     240
gatggttgtt tgactggttc tgttactatt tgccaggtg gtaaacctgt tattatctac      300
actggtggag ataaagatca acaccaagct caaaacattg cttttcccaa agaatagatct     360 gatccttatt tgagagaatg gattaaagct gctaacaatc cagttttgag accagatgaa     420
cctggtatga actctattga gtttagagat ccaactactg gttggattgg tcctgatggt     480
ttgtggagaa tggctgttgg tggtgaattg aacggttact ctgctgcttt gttgtataag     540
tctgaggatt tcttgaattg gactaaagtt gatcatcctt tgtattctca acaggttct      600 aatatgtggg agtgtccaga tttctttgct gttttgcctg gtaacaatgc tggtttggat     660
ttgtctgctg ctattccaca aggtgctaag catgctttga gatgtctgt tgattctgtt      720 gataagtaca tgatcggtgt ttacgatttg caaagagatg ctttcgttcc tgataacgtt     780
gttgatgata agagattgtg gttgagaatc gattacggta cttttctacgc ttctaagtct     840 ttctttgatt ctaacaaaaa cagaagaatc atctgggggtt ggtctagaga aactgattct     900
ccatctgatg atttggagaa gggttgggct ggttttgcata ctattcctag aactatttgg     960
ttggctgata atggtaaaca attgttgcaa tggccagttg aagagattga atcttttgaga    1020 actaacgaga tttctcacca aggtattgaa ttgaataagg gagatttgtt cgaaattaaa    1080
gaggttgatg cttccaagc tgatgttgaa attggttttg agttggcttc tattgatgat    1140
gctgatccat tcgatccttc ttggttgttg gatccagaaa agcattgtgg agaggctggt    1200
gcttctgttc caggtggtat tggtcctttc ggttttggta ttttggcttc tgataacatg    1260
gatgaacaca ctgaggttta cttcagagtt tacaagtctc aagaaaagta catgttttg    1320 atgtgttctg attttgagaag atcttctttg agaccagatt tggaaaaacc tgcttatggt    1380
ggtttctttg agttcgattt ggaaaaggag agaaagatct ctttgagaac tttgatcgat    1440
agatctgctg ttgagtcttt tggtggtggt ggtagagttt gtattacttc tagagtttac    1500
```

```
ccagctgttt tggctgatgt tggtagagcc catatctacg cttttaacaa tggttctgct    1560
actgttagag ttcctcaatt gtctgcttgg actatgagaa aggctcaagt taatgttgaa    1620
aaaggttggt ctgctatt                                                  1638
```

<210> SEQ ID NO 5
<211> LENGTH: 596
<212> TYPE: PRT
<213> ORGANISM: Artificial Sequence
<220> FEATURE:
<223> OTHER INFORMATION: Fructan 1-exohydrolase precursor (W134L)

<400> SEQUENCE: 5

```
Met Ala Gln Ala Trp Ala Phe Leu Leu Pro Val Leu Val Leu Gly Ser
1               5                   10                  15

Tyr Val Thr Ser Leu Phe Phe Pro Ser Tyr Ile Ser Asn Pro Leu Cys
            20                  25                  30

Gly Gly Asp Gly Gly Arg Ser Leu Phe Leu Cys Ala Gln Ala Pro Lys
        35                  40                  45

Asp Gln Asp Pro Ser Pro Ala Val Ser Thr Met Tyr Lys Thr Ala Phe
    50                  55                  60

His Phe Gln Pro Ala Lys Asn Trp Met Asn Asp Pro Ser Gly Pro Met
65                  70                  75                  80

Tyr Phe Asn Gly Ile Tyr His Glu Phe Tyr Gln Tyr Asn Leu Asn Gly
                85                  90                  95

Pro Ile Phe Gly Asp Ile Val Trp Gly His Ser Val Ser Thr Asp Leu
            100                 105                 110

Val Asn Trp Ile Gly Leu Glu Pro Ala Leu Val Arg Asp Thr Pro Ser
        115                 120                 125

Asp Ile Asp Gly Cys Leu Thr Gly Ser Val Thr Ile Leu Pro Gly Gly
    130                 135                 140

Lys Pro Ile Ile Ile Tyr Thr Gly Gly Asp Ile Asp Gln His Gln Ala
145                 150                 155                 160

Gln Asn Ile Ala Phe Pro Lys Asn Arg Ser Asp Pro Tyr Leu Arg Glu
                165                 170                 175

Trp Ile Lys Ala Pro Asn Asn Pro Val Leu Arg Pro Asp Glu Pro Gly
            180                 185                 190

Met Asn Ser Ile Glu Phe Arg Asp Pro Thr Thr Gly Trp Ile Gly Pro
        195                 200                 205

Asp Gly Leu Trp Arg Met Ala Val Gly Gly Glu Leu Asn Gly Tyr Ser
    210                 215                 220

Ala Ala Leu Leu Tyr Lys Ser Glu Asp Phe Leu Asn Trp Thr Lys Val
225                 230                 235                 240

Asp His Pro Leu Tyr Ser His Asn Gly Ser Asn Met Trp Glu Cys Pro
                245                 250                 255

Asp Phe Phe Ala Val Leu Pro Gly Asn Asn Ala Gly Leu Asp Leu Ser
            260                 265                 270

Ala Ala Ile Pro Gln Gly Ala Lys His Ala Leu Lys Met Ser Val Asp
        275                 280                 285

Ser Val Asp Lys Tyr Met Ile Gly Val Tyr Asp Leu Gln Arg Asp Ala
    290                 295                 300

Phe Val Pro Asp Asn Val Val Asp Arg Arg Leu Trp Leu Arg Ile
305                 310                 315                 320

Asp Tyr Gly Thr Phe Tyr Ala Ser Lys Ser Phe Asp Ser Asn Lys
                325                 330                 335
```

Asn Arg Arg Ile Ile Trp Gly Trp Ser Arg Glu Thr Asp Ser Pro Ser
              340                 345                 350

Asp Asp Leu Glu Lys Gly Trp Ala Gly Leu His Thr Ile Pro Arg Thr
          355                 360                 365

Ile Trp Leu Ala Gly Asp Gly Lys Gln Leu Leu Gln Trp Pro Val Glu
      370                 375                 380

Glu Ile Glu Ser Leu Arg Thr Asn Glu Ile Ser His Gln Gly Ile Glu
385                 390                 395                 400

Leu Asn Lys Gly Asp Leu Phe Glu Ile Lys Glu Val Asp Ala Phe Gln
              405                 410                 415

Ala Asp Val Glu Ile Asp Phe Gly Leu Ala Ser Ile Asp Ala Asp
          420                 425                 430

Pro Phe Asp Pro Ser Trp Leu Leu Asp Pro Glu Lys His Cys Gly Glu
      435                 440                 445

Ala Gly Ala Ser Val Pro Gly Gly Ile Gly Pro Phe Gly Leu Val Ile
          450                 455                 460

Leu Ala Ser Asp Asn Met Asp Glu His Thr Glu Val Tyr Phe Arg Val
465                 470                 475                 480

Tyr Lys Ser Gln Glu Lys Tyr Met Val Leu Met Cys Ser Asp Leu Arg
              485                 490                 495

Arg Ser Ser Leu Arg Pro Asp Leu Glu Lys Pro Ala Tyr Gly Gly Phe
          500                 505                 510

Phe Glu Phe Asp Leu Glu Lys Glu Arg Lys Ile Ser Leu Arg Thr Leu
      515                 520                 525

Ile Asp Arg Ser Ala Val Glu Ser Phe Gly Gly Gly Arg Val Cys
530                 535                 540

Ile Thr Ser Arg Val Tyr Pro Ala Val Leu Ala Asp Val Gly Arg Ala
545                 550                 555                 560

His Ile Tyr Ala Phe Asn Asn Gly Ser Ala Thr Val Arg Val Pro Gln
              565                 570                 575

Leu Ser Ala Trp Thr Met Arg Lys Ala Gln Val Asn Val Glu Lys Gly
          580                 585                 590

Trp Ser Ala Ile
      595

<210> SEQ ID NO 6
<211> LENGTH: 1638
<212> TYPE: DNA
<213> ORGANISM: Artificial Sequence
<220> FEATURE:
<223> OTHER INFORMATION: Fructan 1-exohydrolase precursor (W134L)

<400> SEQUENCE: 6
gatccatctc ctgctgtttc tactatgtac aagactgctt ttcatttcca accagctaaa      60
aactggatga atgatccatc tggtcctatg tactttaacg gtatctacca tgaattctac     120
caatacaact tgaacggtcc tatttttcgga gatattgttt ggggtcactc tgtttctact     180
gatttggtta attggattgg tttggagcca gctttggtta gagatactcc ttctgatatt     240
gatggttgtt tgactggttc tgttactatt ttgccaggtg gtaaacctat tattatctac     300
actggtggag atattgatca acaccaagct caaaacattg cttteccaaa gaatagatct     360 gatccttatt tgagagaatg gattaaagct ccaaacaatc tgttttgag accagatgaa     420 cctggtatga actctattga gtttagagat ccaactactg gttggattgg tcctgatggt     480
ttgtggagaa tggctgttgg tggtgaattg aacggttact ctgctgcttt gttgtataag     540

```
tctgaggatt tcttgaattg gactaaagtt gatcatccat tgtattctca caacggttct    600
aatatgtggg agtgtccaga tttctttgct gttttgcctg gtaacaatgc tggtttggat    660
ttgtctgctg ctattccaca aggtgctaag catgctttga agatgtctgt tgattctgtt    720
gataagtaca tgatcggtgt ttacgatttg caaagagatg ctttcgttcc tgataatgtt    780
gttgatgata aagattgtg gttgagaatc gattacggta ctttctacgc ttctaagtct    840
ttctttgatt ctaacaaaaa cagaagaatc atctggggtt ggtctagaga aactgattct    900
ccatctgatg atttggagaa gggttgggct ggtttgcata ctattcctag aactatttgg    960
ttggctggag atggtaaaca attgttgcaa tggccagttg aagagattga atctttgaga    1020
actaacgaga tttctcacca aggtattgaa ttgaataagg gagatttgtt cgaaattaaa    1080
gaggttgatg ctttccaagc tgatgttgaa attgattttg agttggcttc tattgatgat    1140
gctgatccat tcgatccttc ttggttgttg gatccagaaa agcattgtgg agaggctggt    1200
gcttctgttc caggtggtat tggtcctttc ggtttggtta ttttggcttc tgataacatg    1260
gatgaacaca ctgaggttta cttcagagtt tacaagtctc aagaaaagta catggttttg    1320
atgtgttctg atttgagaag atcttctttg agaccagatt tggaaaaacc tgcttatggt    1380
ggtttctttg agttcgattt ggaaaaggag agaaagatct ctttgagaac tttgatcgat    1440
agatctgctg ttgagtcttt tggtggtggt ggtagagttt gtattacttc tagagtttac    1500
ccagctgttt tggctgatgt tggtagagcc catatctacg cttttaacaa tggttctgct    1560
actgttagag ttcctcaatt gtctgcttgg actatgagaa aggctcaagt taatgttgaa    1620
aaaggttggt ctgctatt                                                  1638

<210> SEQ ID NO 7
<211> LENGTH: 543
<212> TYPE: PRT
<213> ORGANISM: Artificial Sequence
<220> FEATURE:
<223> OTHER INFORMATION: Fructan 1-exohydrolase precursor (W120L)

<400> SEQUENCE: 7

Gln Gln Ile Glu Gln Pro Tyr Arg Thr Gly Tyr His Phe Gln Pro Pro
1               5                   10                  15

Ser Asn Trp Met Asn Asp Pro Asn Gly Pro Met Leu Tyr Gln Gly Val
            20                  25                  30

Tyr His Phe Phe Tyr Gln Tyr Asn Pro Tyr Ala Ala Thr Phe Gly Asp
        35                  40                  45

Val Ile Ile Trp Gly His Ala Val Ser Tyr Asp Leu Val Asn Trp Ile
    50                  55                  60

His Leu Asp Pro Ala Ile Tyr Pro Thr Gln Glu Ala Asp Ser Lys Ser
65                  70                  75                  80

Cys Leu Ser Gly Ser Ala Thr Ile Leu Pro Gly Asn Ile Pro Ala Met
                85                  90                  95

Leu Tyr Thr Gly Ser Asp Ser Lys Ser Arg Gln Val Gln Asp Leu Ala
            100                 105                 110

Trp Pro Lys Asn Leu Ser Asp Pro Phe Leu Arg Glu Trp Val Lys His
        115                 120                 125

Pro Lys Asn Pro Leu Ile Thr Pro Pro Glu Gly Val Lys Asp Asp Cys
    130                 135                 140

Phe Arg Asp Pro Ser Thr Ala Trp Leu Gly Pro Asp Gly Val Trp Arg
145                 150                 155                 160

Ile Val Val Gly Gly Asp Arg Asp Asn Asn Gly Met Ala Phe Leu Tyr
```

```
                    165                 170                 175
Gln Ser Thr Asp Phe Val Asn Trp Lys Arg Tyr Asp Gln Pro Leu Ser
                180                 185                 190

Ser Ala Asp Ala Thr Gly Thr Trp Glu Cys Pro Asp Phe Tyr Pro Val
            195                 200                 205

Pro Leu Asn Ser Thr Asn Gly Leu Asp Thr Ser Val Tyr Gly Gly Ser
        210                 215                 220

Val Arg His Val Met Lys Ala Gly Phe Glu Gly His Asp Trp Tyr Thr
225                 230                 235                 240

Ile Gly Thr Tyr Ser Pro Asp Arg Glu Asn Phe Leu Pro Gln Asn Gly
                245                 250                 255

Leu Ser Leu Thr Gly Ser Thr Leu Asp Leu Arg Tyr Asp Tyr Gly Gln
                260                 265                 270

Phe Tyr Ala Ser Lys Ser Phe Asp Asp Ala Lys Asn Arg Arg Val
            275                 280                 285

Leu Trp Ala Trp Val Pro Glu Thr Asp Ser Gln Ala Asp Asp Ile Glu
        290                 295                 300

Lys Gly Trp Ala Gly Leu Gln Ser Phe Pro Arg Ala Leu Trp Ile Asp
305                 310                 315                 320

Arg Asn Gly Lys Gln Leu Ile Gln Trp Pro Val Glu Glu Ile Glu Glu
                325                 330                 335

Leu Arg Gln Asn Gln Val Asn Leu Gln Asn Lys Asn Leu Lys Pro Gly
                340                 345                 350

Ser Val Leu Glu Ile His Gly Ile Ala Ala Ser Gln Ala Asp Val Thr
            355                 360                 365

Ile Ser Phe Lys Leu Glu Gly Leu Lys Glu Ala Glu Val Leu Asp Thr
        370                 375                 380

Thr Leu Val Asp Pro Gln Ala Leu Cys Asn Glu Arg Gly Ala Ser Ser
385                 390                 395                 400

Arg Gly Ala Leu Gly Pro Phe Gly Leu Leu Ala Met Ala Ser Lys Asp
                405                 410                 415

Leu Lys Glu Gln Ser Ala Ile Phe Phe Arg Val Phe Gln Asn Gln Leu
            420                 425                 430

Gly Arg Tyr Ser Val Leu Met Cys Ser Asp Leu Ser Arg Ser Thr Val
        435                 440                 445

Arg Ser Asn Ile Asp Thr Thr Ser Tyr Gly Ala Phe Val Asp Ile Asp
450                 455                 460

Pro Arg Ser Glu Glu Ile Ser Leu Arg Asn Leu Ile Asp His Ser Ile
465                 470                 475                 480

Ile Glu Ser Phe Gly Ala Gly Gly Lys Thr Cys Ile Thr Ser Arg Ile
            485                 490                 495

Tyr Pro Lys Phe Val Asn Glu Glu Ala His Leu Phe Val Phe Asn
        500                 505                 510

Asn Gly Thr Gln Asn Val Lys Ile Ser Glu Met Ser Ala Trp Ser Met
        515                 520                 525

Lys Asn Ala Lys Phe Val Val Asp Gln Ser Val Lys Ser Ala Ala
530                 535                 540

<210> SEQ ID NO 8
<211> LENGTH: 1629
<212> TYPE: DNA
<213> ORGANISM: Artificial Sequence
<220> FEATURE:
<223> OTHER INFORMATION: Fructan 1-exohydrolase precursor (W120L)
```

<400> SEQUENCE: 8

```
caacaaattg aacaaccata cagaactggt tatcattttc aaccaccttc taactggatg      60
aatgatccaa acggtcctat gttgtaccaa ggtgtttacc acttttttcta ccaatacaac    120
ccttacgctg ctactttcgg agatgttatt atttggggtc atgctgtttc ttacgatttg    180
gttaactgga ttcacttgga tccagctatc taccctactc aagaagctga ttctaagtct    240
tgtttgtctg gttctgctac tattttgcca ggtaatattc ctgctatgtt gtatactggt    300
tctgattcta agtctagaca agttcaagat ttggcttggc aaagaacttg tctgatcca     360
tttttgagag aatgggttaa gcatccaaag aacccttttga ttactccacc tgagggtgtt   420
aaggatgatt gtttcagaga tccatctact gcttggttgg gtcctgatgg tgtttggaga    480
attgttgttg gtggagatag agataacaat ggtatggctt tcttgtacca atctactgat    540
ttcgttaact ggaaaagata tgatcaacca ttgtcttctg ctgatgctac tggtacttgg    600
gaatgtcctg attttacccc agttcctttg aattctacta acggtttgga tacttctgtt   660
tatggtggtt ctgttagaca tgttatgaaa gctggttttg aaggtcacga ttggtacact    720
attggtactt attctccaga tagagagaat ttcttgcctc aaaacggttt gtctttgact    780
ggttctactt tggatttgag atacgattat ggtcaatttt acgcttctaa gtctttctt    840
gatgatgcta aaaatagaag agttttgtgg gcttgggttc cagaaactga ttctcaagct    900
gatgatattg agaagggttg ggctggtttg caatctttcc aagagctttt gtggatcgat    960
agaaacggta acaattgat ccaatggcct gttgaagaga ttgaagagtt gagacaaaac    1020
caagttaact tgcaaaacaa gaatttgaaa ccaggttctg ttttggaaat tcacggtatt    1080
gctgcttctc aagctgatgt tactatctct tttaagttgg agggtttgaa agaagctgag   1140
gttttggata ctactttggt tgatccacaa gctttgtgta tgaaagagg tgcttcttct    1200
agaggtgctt tgggtccttt tggtttgttg gctatggctt ctaaggattt gaaggagcaa    1260
tctgctattt tctttagagt tttccaaaac caattgggta gatactctgt tttgatgtgt   1320
tctgatttgt ctagatctac tgttagatct aacatcgata ctacttctta tggtgctttt    1380
gttgatattg atccaagatc tgaagagatc tctttgagaa acttgatcga tcattctatc    1440
atcgaatctt tcggtgctgg tggtaaaact tgtatcactt ctagaatcta ccctaagttc    1500
gttaacaatg aagaggctca cttgttcgtt ttcaacaacg gtactcaaaa cgttaagatc    1560
tctgagatgt ctgcttggtc tatgaagaac gctaagttcg ttgttgatca atctgttaag    1620
tctgctgct                                                            1629
```

<210> SEQ ID NO 9
<211> LENGTH: 6
<212> TYPE: PRT
<213> ORGANISM: Artificial Sequence
<220> FEATURE:
<223> OTHER INFORMATION: Fructan 1-exohydrolase precursor
<220> FEATURE:
<221> NAME/KEY: MISC_FEATURE
<222> LOCATION: (1)..(2)
<223> OTHER INFORMATION: Xaa is a non aromatic amino acid

<400> SEQUENCE: 9

Xaa Xaa Gly Ser Ala Thr
1               5

<210> SEQ ID NO 10
<211> LENGTH: 6
<212> TYPE: PRT

-continued

```
<213> ORGANISM: Artificial Sequence
<220> FEATURE:
<223> OTHER INFORMATION: Fructan 1-exohydrolase precursor

<400> SEQUENCE: 10

Leu Ser Gly Ser Ala Thr
1               5

<210> SEQ ID NO 11
<211> LENGTH: 4
<212> TYPE: PRT
<213> ORGANISM: Artificial Sequence
<220> FEATURE:
<223> OTHER INFORMATION: Fructan 1-exohydrolase precursor
<220> FEATURE:
<221> NAME/KEY: MISC_FEATURE
<222> LOCATION: (4)..(4)
<223> OTHER INFORMATION: Xaa is selected from the group consisting of
      serine, leucine, isoleucine, and valine

<400> SEQUENCE: 11

Tyr Thr Gly Xaa
1

<210> SEQ ID NO 12
<211> LENGTH: 4
<212> TYPE: PRT
<213> ORGANISM: Artificial Sequence
<220> FEATURE:
<223> OTHER INFORMATION: Fructan 1-exohydrolase precursor

<400> SEQUENCE: 12

Tyr Thr Gly Ser
1
```